United States Patent [19]

Schlosser et al.

[11] Patent Number: 5,562,859
[45] Date of Patent: Oct. 8, 1996

[54] 2-FLUOROPYRAZINES PROCESS FOR THEIR PREPARATION, AND THEIR USE IN LIQUID-CRYSTALLINE MIXTURES

[75] Inventors: Hubert Schlosser, Glashütten, Germany; Gerd Illian, Tokyo, Japan; Anke Kaltbeitzel, Rüsselsheim; Rainer Wingen, Hattersheim am Main, both of Germany

[73] Assignee: Hoechst Aktiengesellschaft, Germany

[21] Appl. No.: 457,747

[22] Filed: Jun. 1, 1995

Related U.S. Application Data

[63] Continuation of Ser. No. 354,940, Dec. 13, 1994, abandoned, which is a continuation of Ser. No. 929,945, Aug. 14, 1992, abandoned.

[30] Foreign Application Priority Data

Aug. 17, 1991 [DE] Germany .................. 41 27 306.0

[51] Int. Cl.$^6$ .................. C09K 19/34; C07D 237/00; C07D 241/00; G02F 1/13
[52] U.S. Cl. .................. 252/299.61; 544/224; 544/336; 359/104
[58] Field of Search .................. 252/299.61; 544/224, 544/336; 359/104

[56] References Cited

FOREIGN PATENT DOCUMENTS

| | | |
|---|---|---|
| 265421 | 11/1965 | Australia . |
| 0158137 | 10/1985 | European Pat. Off. . |
| 0284093 | 9/1988 | European Pat. Off. . |
| 0394464 | 10/1990 | European Pat. Off. . |
| 3411-571-A | 4/1984 | Germany . |
| 3919-104-A | 6/1989 | Germany . |
| 475-444-A | 9/1990 | Germany . |
| 4029165 | 3/1992 | Germany . |
| 0059726 | 5/1981 | Japan . |
| 6-1129-171-A | 11/1984 | Japan . |
| 61129171 | 11/1984 | Japan . |
| 61-129171 | 6/1986 | Japan . |
| 02169537 | 12/1988 | Japan . |
| 2-169537 | 6/1990 | Japan . |
| 2175409 | 11/1986 | United Kingdom . |
| 90/15116 | 12/1990 | WIPO . |
| 91/04249 | 4/1991 | WIPO . |
| 91/04248 | 4/1991 | WIPO . |

OTHER PUBLICATIONS

Radiation Chem., Photochem., vol. 113, 1990, p. 643; 113: 181632c "Non–chiral fluorobinphenyl derivatives as smectic liquid crystals and ferroelectric liquid–crystal compositions containing them", Kanto Chemical Co., Ltd., equivalent to Japanese Abstract 02,169,537.
Crystallogr, Liquid Crystals, vol. 106, 1987, p. 507, 106: 26206d "Phenylpyrazine derivatives", Ube Industries, Ltd., equivalent to Japanese Abstract 61,129,171.
V. Reiffenrath et al., New Liquid Crystalline Compounds with Negative Dielectric Anisotropy, 1988, p. 54.
D. Demus et al., Fl. Kristalle in Tabellen, pp. 263–266, 1988.

*Primary Examiner*—C. H. Kelly
*Attorney, Agent, or Firm*—Curtis, Morris & Safford, P.C.

[57] ABSTRACT

2-Fluoropyrazines, process for their preparation, and their use in liquid-crystalline mixtures
A 2-fluoropyrazine of the formula (I)

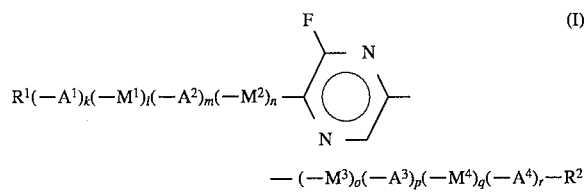

in which the symbols have the following meanings:
$R^1$ and $R^2$, independently of one another, are, for example, H or straight-chain or branched alkyl,
$A^1$, $A^2$, $A^3$ and $A^4$ are identical or different and are, for example, 1,4-phenylene or
$M^1$, $M^2$, $M^3$ and $M^4$ are identical or different and are, for example, —O— or —CO—O—,
$R^3$, $R^4$, $R^6$ and $R^7$, independently of one another, are, for example, H or straight-chain or branched alkyl,
$M^5$ is, for example, —O—CO— or a single bond,
k, l, m, n, o, p, q and r are zero or one, with the condition that the sum of k+m+p+r is less than 4 and greater than zero,
can advantageously be employed as a component in liquid-crystal mixtures.

16 Claims, No Drawings

2-FLUOROPYRAZINES PROCESS FOR THEIR PREPARATION, AND THEIR USE IN LIQUID-CRYSTALLINE MIXTURES

DESCRIPTION

This application is a continuation of application Ser. No. 08/354,940, filed Dec. 13, 1994, now abandoned which is a continuation of application Ser. No. 07/929,945, filed Aug. 14, 1992, now abandoned.

The unusual combination of anisotropic and fluid behavior of liquid crystals has resulted in their use in electro-optical switching and display devices, where their electrical, magnetic, elastic and/or thermal properties can be utilized to effect changes in alignment. Optical effects can be achieved, for example, with the aid of birefringence, the inclusion of dye molecules which absorb dichroically ("guest-host mode") or light scattering.

In order to satisfy the constantly increasing demands of practice in the various areas of application, there is a constant demand for novel improved liquid-crystal mixtures and thus also for a large number of mesogenic compounds of various structures. This applies both to areas in which nematic LC phases are used, and to those in which smectic LC phases are used.

There has been considerable interest in recent years in ferroelectric liquid-crystalline mixtures (FLC mixtures) (see, for example, Lagerwall et al., "Ferroelectric Liquid Crystals for Displays", SID Symposium, October Meeting 1985, San Diego, Calif., USA). For practical use of ferroelectric liquid crystals in electro-optical displays, chiral, tilted smectic phases, such as $S_c^*$ phases, are required [see R. B. Meyer, L. Liebert, L. Strzelecki and P. Keller, J. Physique 36, L-69 (1975)], which are stable over a broad temperature range. This object can be achieved by means of compounds which themselves form such phases, for example $S_c^*$ phases, or by doping compounds which form non-chiral, tilted smectic phases with optically active compounds [see M. Brunet, C. Williams, Ann. Phys. 3, 237 (1978)].

If ferroelectric liquid-crystalline mixtures are used in electro-optical components, a uniform planar alignment of liquid crystals is necessary to achieve a high contrast ratio. It has been found that a uniform planar alignment in the $S_c$ phase can be achieved if the phase sequence of the liquid-crystal mixture is, with decreasing temperature: isotropic→nematic→smectic A→smectic C (see, for example, K. Flatischler et al., Mol. Cryst. Liq. Cryst. 131, 21 (1985); T. Matsumoto et al., p. 468–470, Proc. of the 6th Int. Display Research Conf., Japan Display, 30 September-2 October 1986, Tokyo, Japan; M. Murakami et al., ibid., p. 344–347).

For ferroelectric (chiral smectic) liquid-crystal mixtures, it is additionally necessary for the condition to be fulfilled that the pitch of the helix in the $S_c^*$ phase is large, i.e. greater than 5 µm, and that in the N* phase is very large, i.e. greater than 10 µm, or infinite.

The optical response time τ[µs] of ferroelectric liquid-crystal systems, which should be as short as possible, depends on the rotational viscosity of the system γ[mPas], the spontaneous polarization $P_s$[nC/cm$^2$] and the electrical field strength E[V/m], in accordance with the equation $$T \approx \frac{v}{P_s \cdot E}$$

Since the field strength E is determined by the electrode separation in the electro-optical component and by the applied voltage, the ferroelectric display medium must have low viscosity and high spontaneous polarization in order to achieve a short response time.

Finally, in addition to thermal, chemical and photochemical stability, low optical anisotropy Δn, preferably of ≈ 0.13, and low positive or preferably negative dielectric anisotropy Δε are required (see S. T. Lagerwall et al., "Ferroelectric Liquid Crystals for Displays", SID Symposium, Oct. Meeting 1985, San Diego, Calif., USA).

It is generally only possible to satisfy all these conditions together by means of mixtures of more than one component. The base (or matrix) used here preferably comprises compounds which as far as possible themselves already have the desired phase sequence I→N→$S_A$→$S_c$. Further components of the mixture are frequently added in order to depress the melting point and to broaden the $S_c$ and usually also the N phase, to induce optical activity, for pitch compensation and for matching of the optical and dielectric anisotropies, but if possible the rotational viscosity, for example, should not be increased.

Some of these components and also certain mixtures are already known from the prior art. However, since the development of, in particular, ferroelectric liquid-crystal mixtures can in no way be regarded as complete, the manufacturers of displays are interested in different mixtures, partly also because only the interaction of the liquid-crystal mixtures with the individual components of the display device or of the cells (for example the alignment layer) allows conclusions to be drawn on the quality of, in addition, the liquid-crystalline mixtures.

EP-B 0 158 137 describes 4-fluoropyrimidines as compounds and as mixture components in general. In general, they have only a slight tendency, if any at all, toward the formation of smectic phases.

DE-A 40 29 165 and DE-A 40 30 582 present 4-fluoropyrimidines as components of ferroelectric liquid-crystal mixtures.

It is furthermore known that mono- and difluorophenyl compounds can be used as components of liquid-crystal mixtures (JP-A 2169-537; V. Reiffenrath, The Twelfth International Liquid Crystal Conference, Freiburg, 15–19 August 1988). However, some of these compounds do not have an $S_c$ phase. Furthermore, fluorophobic interactions frequently cause miscibility problems with structurally different mixture components, for example phenylpyrimidines.

Pyrazine derivatives likewise have a liquid-crystalline behavior with formation of an $S_c$ phase (D. Demus, H. Demus, H. Zaschke, Flüssige Kristalle in Tabellen [Liquid Crystals in Tables], VEB Deutscher Verlag für Grundstoffindustrie, Leipzig, 1974; JP 61/129,171-A). However, an $S_B$ phase which frequently occurs in these compounds and high phase-transition temperatures impair their use in liquid-crystal mixtures.

The present invention relates to novel 2-fluoropyrazine derivatives and their use as components of liquid-crystal mixtures, in particular for ferroelectric mixtures, at least one 2-fluoropyrazine of the formula (I) being employed as a component in a liquid-crystal mixtures.

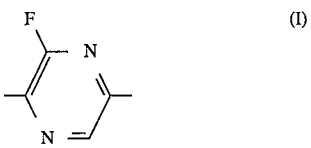

$$R^1(-A^1)_k(-M^1)_l(-A^2)_m(-M^2)_n \quad (I)$$

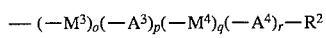

The symbols in this formula have the following meanings:

$R^1$ and $R^2$ are, independently of one another, H, F, Cl, CN, NCS, —CF$_3$, —OCF$_3$, —OCHF$_2$ or straight-chain or branched alkyl having 1 to 16 carbon atoms (with or without an asymmetrical carbon atom), it also being possible for one or two non-adjacent —CH$_2$— groups each to be replaced by —O—, —S—, —CO—, —CO—O—, —O—CO—, —CO—S—, —S—CO—, —O—CO—O—, —CH=CH—, —C≡C—,

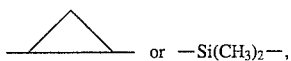

and it also being possible for one or more hydrogen atoms of the alkyl radical each to be substituted by F, Cl, Br and/or CN, or one of the following chiral groups:

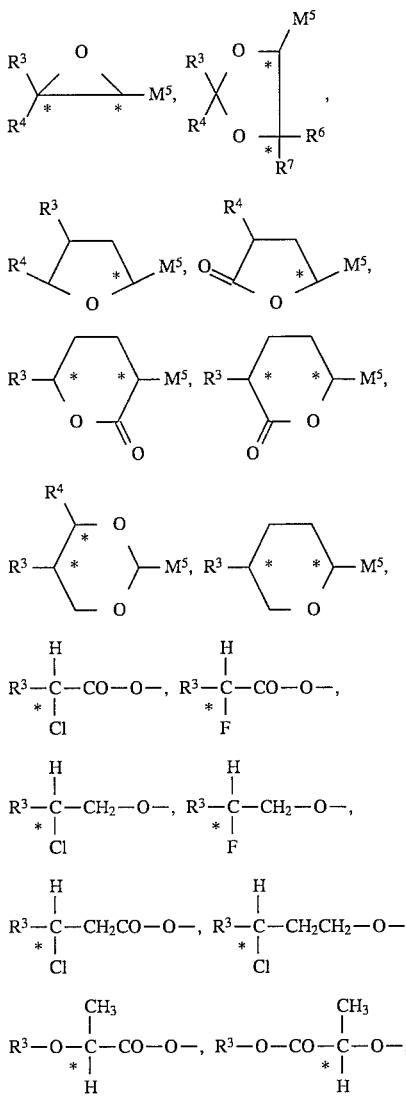

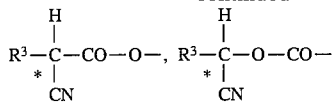

$A^1$, $A^2$, $A^3$ and $A^4$ are identical or different 1,4-phenylene, pyrazine-2,5-diyl, pyridazine-3,6-diyl, pyridine-2,5-diyl or pyrimidine-2,5-diyl, it being possible for one or two hydrogen atoms to be replaced by F, Cl and/or CN, or are trans-1,4-cyclohexylene, in which one or two hydrogen atoms may be replaced by CN and/or CH$_3$, or are 1,3,4-thiadiazole-2,5-diyl, 1,3-dioxane-2,5-diyl, naphthalene-2,6-diyl, bicyclo[2.2.2]octane-1,4-diyl or 1,3-dioxa-borinane-2,5-diyl;

$M^1$, $M^2$, $M^3$ and $M^4$ are identical or different —O—, —S—, —CO—, —CO—O—, —O—CO—, —CO—S—, —S—CO—, —O—CO—O—, —CH$_2$—O—, —O—CH$_2$—, —CH$_2$—CH$_2$—, —CH=CH— or —C≡C—;

$R^3$, $R^4$, $R^6$ and $R^7$ independently of one another, are H or straight-chain or branched alkyl having 1 to 16 carbon atoms;

or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond; and k, l, m, n, o, p, q and r are zero or 1, with the condition that the sum of k+m+p+r is less than 4 and greater than zero.

In a preferred embodiment of the invention, the symbols have the following meanings:

$R^1$ and $R^2$, independently of one another, are H, F, CN or straight-chain or branched alkyl having 1 to 16 carbon atoms (with or without an asymmetrical carbon atom), it also being possible for a —CH$_2$— group to be replaced by —O—, —S—, —CO—, —CO—O—, —O—CO—, —O—CO—O—, —CH=CH—, —C≡C—,

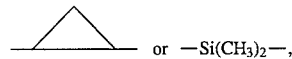

or one of the following chiral groups:

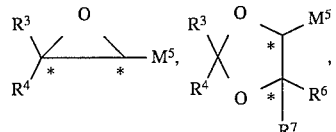

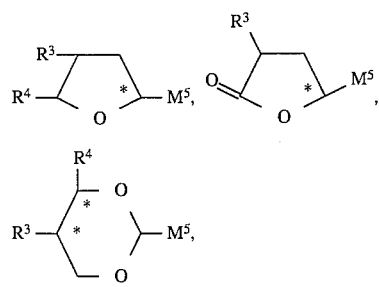

-continued

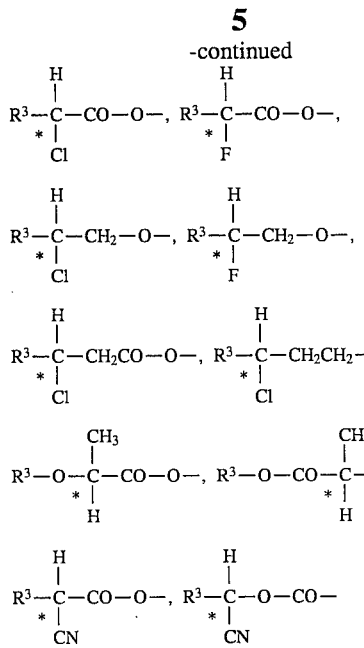

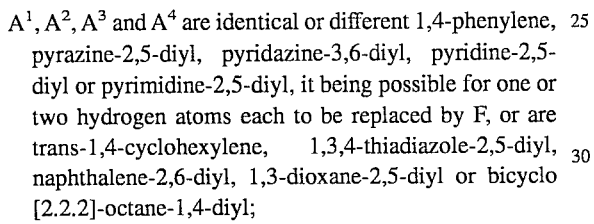

$A^1$, $A^2$, $A^3$ and $A^4$ are identical or different 1,4-phenylene, pyrazine-2,5-diyl, pyridazine-3,6-diyl, pyridine-2,5-diyl or pyrimidine-2,5-diyl, it being possible for one or two hydrogen atoms each to be replaced by F, or are trans-1,4-cyclohexylene, 1,3,4-thiadiazole-2,5-diyl, naphthalene-2,6-diyl, 1,3-dioxane-2,5-diyl or bicyclo[2.2.2]-octane-1,4-diyl;

$M^1$, $M^2$, $M^3$ and $M^4$ are identical or different —O—, —CO—, —CO—O—, —O—CO—, —CH$_2$—O—, —O—CH$_2$—, —CH$_2$—CH$_2$—, —CH=CH— or —C≡C—;

$R^3$, $R^4$, $R^6$ and $R^7$, independently of one another, are H or straight-chain or branched alkyl having 1 to 16 carbon atoms; $R^3$ and $R^4$ together are alternatively —(CH$_2$)$_4$— or —(CH$_2$)$_5$— if bonded as substituents to a dioxolane system; and $M^5$ is —CH$_2$—O—, —CO—O—, —O—CH$_2$—, —O—CO— or a single bond.

Particular preference is given to 2-fluoropyrazine derivatives in which the symbols have the following meanings:

$R^1$ and $R^2$, independently of one another, are H, F, CN or straight-chain or branched alkyl having 1 to 16 carbon atoms (with or without an asymmetrical carbon atom), it also being possible for a —CH$_2$— group to be replaced by —O—, —CO—, —CO—O—, —O—CO—, —CH=CH—,

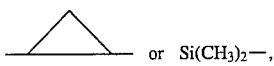 or Si(CH$_3$)$_2$—, or one of the following chiral groups:

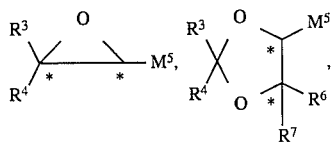

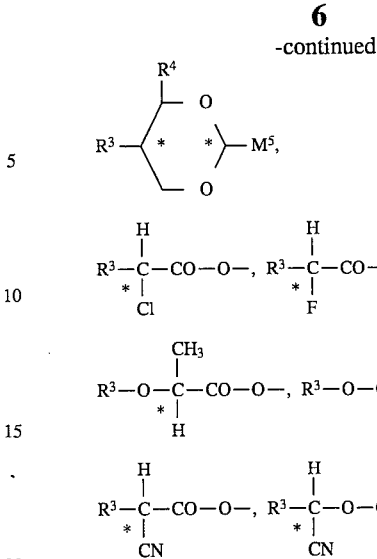

$A^1$, $A^2$, $A^3$ and $A^4$ are identical or different 1,4-phenylene, pyrazine-2,5-diyl, pyridazine-3,6-diyl, pyridine-2,5-diyl or pyrimidine-2,5-diyl, in which a hydrogen atom may be replaced by F, or are trans-1,4-cyclohexylene, naphthalene-2,6-diyl or 1,3-dioxane-2,5-diyl;

$M^1$, $M^2$, $M^3$ and $M^4$ are identical or different —O—, —CO—O—, —O—CO—, —O—CH$_2$—, —CH$_2$—O—, —CH$_2$—CH$_2$— or —CH=CH—;

$R^3$, $R^4$, $R^6$ and $R^7$, independently of one another, are H or straight-chain or branched alkyl having 1 to 16 carbon atoms; $R^3$ and $R^4$ together are alternatively —(CH$_2$)$_4$— or —(CH$_2$)$_5$— if bonded as substituents to a dioxolane system; and $M^5$ is —CH$_2$—O—, —CO—O—, —O—CH$_2$—, —O—CO— or a single bond.

Particular preference is given to a 2-fluoropyrazine in which $R^1$ and $R^2$, independently of one another, are H or alkyl having 1 to 16 carbon atoms, it being possible for a —CH$_2$— group to be replaced by —O—, or the, chiral group

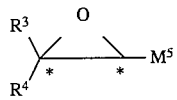

$A^1$, $A^2$, $A^3$ and $A^4$ are identical or different 1,4-phenylene, pyrimidine-2,5-diyl or 1,4-cyclohexylene, $M^1$, $M^2$, $M^3$ and $M^4$ are identical or different —O—, —COO—, —CH$_2$—O— or —O—CH$_2$—, $M^5$ is —CH$_2$O— or —COO—, and $R^3$ and $R^4$, independently of one another, are H or straight-chain alkyl having 1 to 10 carbon atoms.

The 2-fluoropyrazines are chemically and photochemically stable. In contrast to the previously known pyrazine derivatives (see above), the compounds according to the invention have low phase-transition temperatures which favor their use in liquid-crystal mixtures. Some of them have broad $S_A$ phases, so that the range of the $S_A$ phase can be increased or an $S_A$ phase can be generated by adding these compounds to liquid-crystalline mixtures. In this way, the ability of the mixture to be aligned in a cell can be improved. A broad $S_A$ phase can in addition slightly reduce the switching angle $\theta_{off}$ of a ferroelectric liquid-crystal mixture and thus increase its response speed.

The compounds according to the invention may also have an $S_c$ and N phase.

The 2-fluoropyrazine compounds can be combined with a large number of other liquid crystals to give ferro-electric liquid-crystal mixtures, for example with phenylpyrimidines, phenylpyridines, phenylbenzoates, naphthalene compounds, biphenyl derivatives and thiadiazoles.

The compounds according to the invention are also particularly suitable for blending with difluorophenyl, fluoropyridine or thiadiazole compounds, since these likewise have a large negative $\Delta\epsilon$. Mixtures in which re-relaxation of the director after switching can be prevented by AC field stabilization can be produced on this basis.

Liquid-crystalline mixtures which contain compounds of the formula (I) are particularly suitable for use in electro-optical switching and display devices (displays). Switching and display devices (LC displays) contain, inter alia, the following constituents: a liquid-crystalline medium, outer plates (for example made of glass or plastic), coated with transparent electrodes, at least one alignment layer, spacers, adhesive frames, polarizers and, for color displays, thin colored filter layers. Further possible components are antireflection, passivation, compensation and barrier layers and electrically nonlinear elements, such as thin-film transistors (TFTs) and metal-insulator-metal (MIM) elements. The structure of liquid-crystal displays has already been described in detail in relevant monographs (for example E. Kaneko, "Liquid Crystal TV Displays: Principles and Applications of Liquid Crystal Displays", KTK Scientific Publishers, 1987, pages 12–30 and 163–172).

The compounds I according to the invention can be prepared by processes shown in Schemes 1 to 4, in which the side chains $R^1(-A^1)_k(-M^1)_1(-A^2)_m(-M^2)_n$ and $(-M^3)_o(-A^3)_p(-M^4)_q(-A^4)_r-R^2$ are introduced into the 3- or 6-position of the pyrazine ring by a multistep reaction starting from 2,6-dichloropyrazine (II).

The starting compound for this process is 2,6-dichloropyrazine (II), which is commercially available and gives 2,6-difluoropyrazine (III) by reaction with from 3 to 20, in particular from 5 to 10, mol equivalents of a fluoride reagent, such as silver fluoride, sodium fluoride, potassium fluoride or cesium fluoride, at temperatures between 50° and 200° C., in particular between 100° and 150° C., using catalytic amounts (from 1 to 20 mol percent, in particular from 5 to 15 mol percent), of at at least one complexing agent, such as 18-crown-6, dibenzo-18-crown-6 or 1,10-diaza-4,7,13,16,21,24-hexaoxa-bicyclo[8.8.8]hexacosane.

Replacement of a fluorine substituent in (III) by a group of the formula $Z^2=(-M^3)_o(A^3)_p(M^4)_q(A^4)_r-R^2$ by reaction with a metal compound of $Z^2$ for example a lithium, sodium, potassium or magnesium compound, at temperatures between −40° and 100° C., in particular between −10° and 70° C., in an inert reaction medium, for example diethyl ether, tetrahydrofuran, 1,4-dioxane, ethylene glycol diethyl ether or diethylene glycol diethyl ether, gives compounds of the formula (V).

Reaction of 2,6-dichloropyrazine with from 1 to 3, in particular from 1.5 to 2.5, mol equivalents of one of the abovementioned fluoride reagents at temperatures between 50° and 200° C., in particular between 100° and 150° C., and at a pressure between 50 and 300 mmHg, in particular between 100 and 200 mmHg, using catalytic amounts (from 1 to 20 mol percent, in particular from 5 to 15 mol percent) of one of the abovementioned complexing agents gives 2-chloro-6-fluoropyrazine (IV).

Cross-coupling of compound (IV) with organometallic derivatives of $Z^2$, for example Grignard, lithium and zinc derivatives, and boronic acids of $Z^2$ using transition-metal catalysts, for example dichloro[1,3-bis(diphenylphosphino)-propane]nickel(II) and tetrakis(triphenylphosphine)-palladium(0), at temperatures between −40° and 200° C., in particular between −10° and 100° C., in reaction media such as benzene/ethanol/water for the reaction with boronic acids of $Z^2$ and, for example, diethyl ether or tetrahydrofuran for the reaction with Grignard, lithium and zinc derivatives of $Z^2$, likewise gives compounds of type (V).

2-Fluoropyrazines of type (V) can be converted into 2-fluoro-3-lithiopyrazines of the formula (VI) by treatment with a lithium compound, for example an alkyllithium compound or a lithium amide, at temperatures between −40° and −100° C., in particular between −60° and −80° C., in an inert reaction medium, for example diethyl ether, tetrahydrofuran or ethylene glycol diethyl ether. 3-Lithiopyrazines of the formula (VI) undergo reaction with electrophilic compounds, enabling 2-fluoropyrazines of the formula (I) to be obtained either directly or via further intermediates (compounds of the formula (VII), (VIII), (IX), (X), (XI) and (XII)).

Thus, reaction of compounds of type (VI) with nitriles, carboxylic acid halides and formylmethyl derivatives of $Z^3$ at temperatures between −40° and −100° C., in particular between −60° and −80° C., in an inert reaction medium, for example diethyl ether, tetrahydrofuran or ethylene glycol diethyl ether, gives 2-fluoropyrazines of the formula (I) directly. Olefinic 2-fluoropyrazines (I) can be converted into saturated species (I) by hydrogenation of the olefinic double bond by methods known per se from the literature (see, for example, Houben-Weyl, Methoden der Organischen Chemie [Methods of Organic Chemistry], Georg Thieme Verlag, Stuttgart).

Reaction of 2-fluoro-3-lithiopyrazines (VI) with halogens, for example chlorine, bromine or iodine, at temperatures between −40° and −100° C., in particular between −60° and −80° C., in an inert reaction medium, for example diethyl ether, tetrahydrofuran or ethylene glycol diethyl ether, gives 2-fluoro-3-halopyrazines of the formula (VII). Cross-coupling of compounds of type (VII) with organometallic derivatives of $Z^1$, for example Grignard, lithium and zinc derivatives, and boronic acids of $Z^1$ using transition-metal catalysts, for example dichloro-[1,3-bis(diphenylphosphino)propane]nickel(II) and tetrakis(triphenylphosphine)palladium(0), at temperatures between −40° and 200° C., in particular between −10° and 100° C., in reaction media such as benzene/ethanol/water for the reaction with boronic acids of $Z^1$ and, for example, diethyl ether or tetrahydrofuran for the reaction with Grignard, lithium and zinc derivatives of $Z^1$, gives 2-fluoropyrazines (I).

Treatment of 2-fluoro-3-lithiopyrazines (VI) with carbon dioxide at temperatures between −40° and −100° C., in particular between −60° and −80° C., in an inert reaction medium, for example diethyl ether, tetrahydrofuran or ethylene glycol diethyl ether, gives 2-fluoro-3-pyrazinecarboxylic acids of the formula (VIII). The species (VIII) can be converted by methods known per se from the literature (see, for example, Houben-Weyl, Methoden der Organischen Chemie [Methods of Organic Chemistry], Georg Thieme Verlag, Stuttgart), either directly by esterification using alcohols of $Z^3$ with the aid of suitable condensation agents, for example carbodiimides, to give 2-fluoropyrazines (I), or after reduction to 2-fluoro-3-hydroxymethylpyrazines (IX) using suitable reducing agents, for example complex hydrides, by esterification using carboxylic acids or carboxylic acid halides of $Z^3$ or etherification using alcohols or halides of $Z^3=R^1(-A^1)_k(-M^2)_1(-A^2)m$ to give compounds of the formula I.

Reaction of 2-fluoro-3-lithiopyrazines (VI) with formamides at temperatures between −40° and −100° C., in particular between −60° and −80° C., in an inert reaction medium, for example diethyl ether, tetrahydrofuran or ethylene glycol diethyl ether, gives 2-fluoro-3-formylpyrazines (X), which, after acid-catalyzed acetalization using 2-$Z^4$-1, 3-propanediols by methods known per se from the literature (see, for example, Houben-Weyl, Methoden 15 der Organischen Chemie [Methods of Organic Chemistry], Georg Thieme Verlag, Stuttgart), give 2-fluoropyrazines of type (I).

Successive treatment of 2-fluoro-3-lithiopyrazines (VI) with trialkyl borates at temperatures between −40° and −100° C., in particular between −60° and −80° C., and aqueous acid at temperatures between −10° and 50° C., in particular between 10° and 30° C., in an inert reaction medium, for example diethyl ether, tetrahydrofuran or ethylene glycol diethyl ether, gives 2-fluoro-3-pyrazineboronic acids of the formula (XI).

The boronic acids (XI) can be subjected to coupling reactions with halides of $Z^1$ using a transition-metal catalyst, for example tetrakis(triphenylphosphine)-palladium(0), at temperatures between 30° and 200° C., in particular between 50° and 100° C., in reaction media such as benzene/ethanol/water, to prepare compounds of type (I).

2-Fluoropyrazines (I) are furthermore obtained from the boronic acids (XI) by esterification of the latter using 2-$Z^4$-1,3-propanediols ($Z^4$=$R^1$(−$A^1$)$_k$(−$M^1$)$_1$) by methods known per se from the literature (see, for example, Houben-Weyl, Methoden der Organischen Chemie [Methods of Organic Chemistry ], Georg Thieme Verlag, Stuttgart).

Oxidation of the boronic acids (XI) using peroxides, for example hydrogen peroxide, at temperatures between 10° and 100° C., in particular between 30° and 70° C., in reaction media such as diethyl ether or tetrahydrofuran gives 2-fluoro-3-hydroxypyrazines (XII), which can be converted into 2-fluoropyrazines of the formula (I) by methods known per se from the literature (see, for example, Houben-Weyl, Methoden der Organischen Chemie [Methods of Organic Chemistry], Georg Thieme Verlag, Stuttgart) by esterification using carboxylic acids or carboxylic halides of $Z^3$ of by etherification using alcohols or halides of $Z^3$.

Scheme 1:

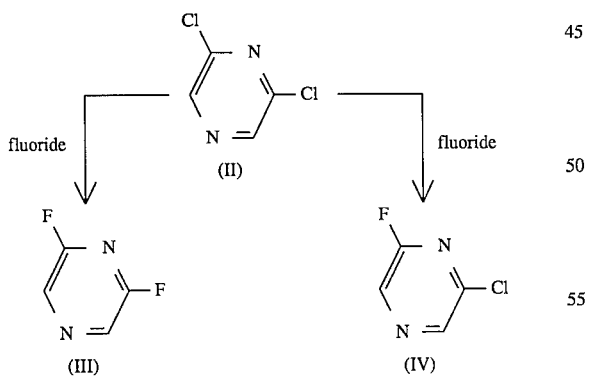

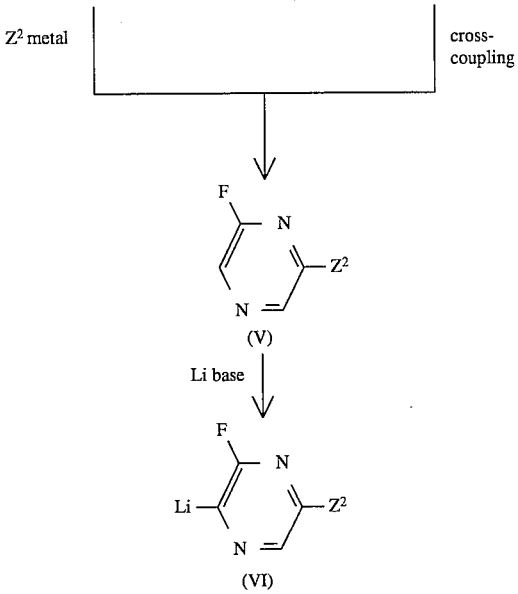

$Z^2$=(−$M^3$)$_o$(−$A^3$)$_p$(−$M^4$)$_q$(−$A^4$)$_r$−$R^2$

Scheme 2:
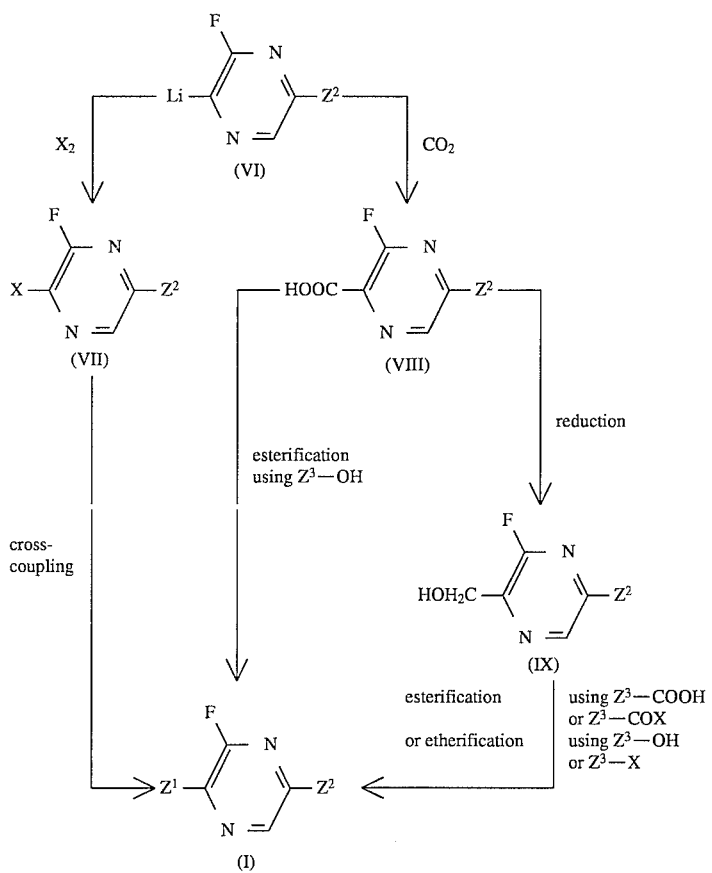
$Z^1=R^1(-A^1)_k(-M^1)_l(-A^2)_m(M^2)_n;$  $Z^2$=see scheme 1
$Z^3=R^1(-A^1)_k(-M^2)_l(-A^2)_m;$  X=Cl, Br, I
Scheme 3:
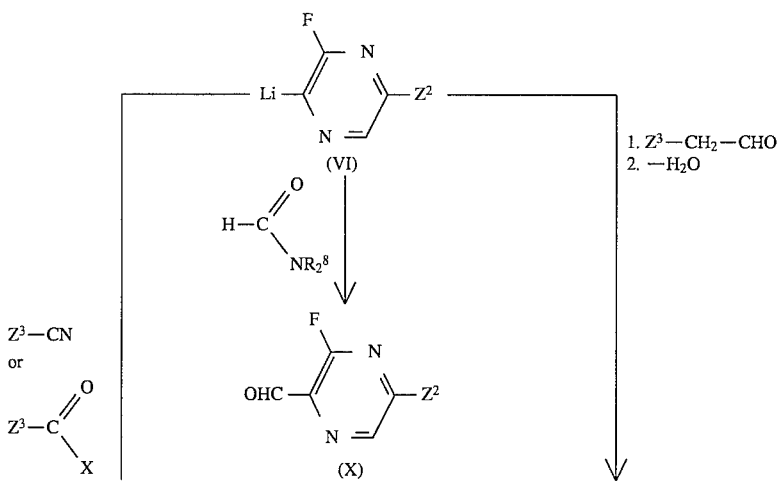

-continued
Scheme 3:
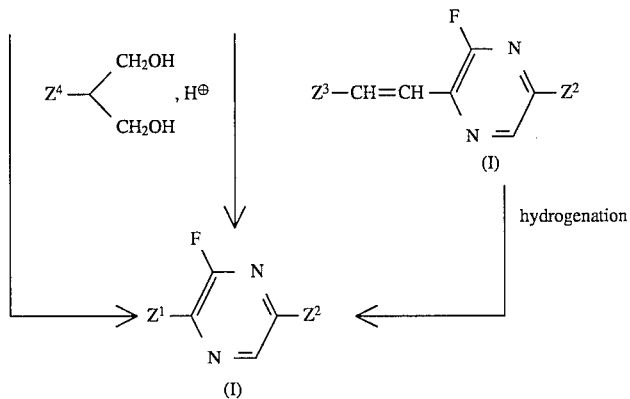
$Z^1, Z^2, Z^3, X$ = see schemes 1 and 2
$Z^4 = R^1(-A^1)_k(-M^1)_l$
$R^8$ = straight-chain or branched alkyl having 1 to 16 carbon atoms
Scheme 4:
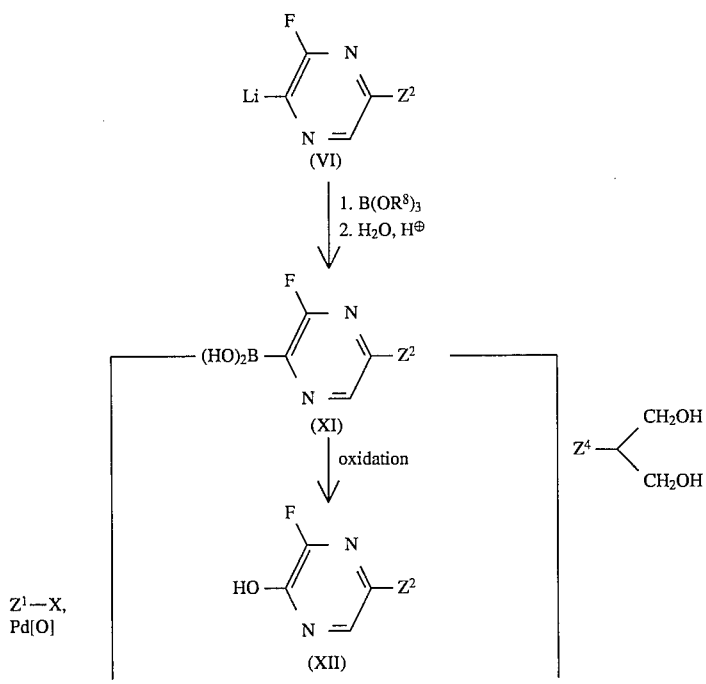

-continued
Scheme 4:

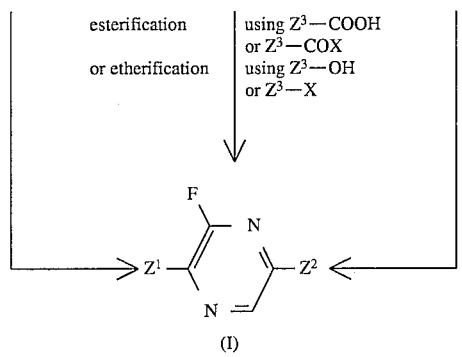

$Z^1$, $Z^2$, $Z^3$, $Z^4$, X, $R^8$ see schemes 1, 2 and 3

The invention is described in greater detail by means of the examples below:

For the ferroelectric liquid-crystal mixtures, the values for the spontaneous polarization $P_s[nC/cm^2]$, the electrical response time $\tau[\mu s]$ and the helical twisting power in the nematic phase were determined, the first two measurements being carried out at a temperature of 20° C.

The $P_s$ values were measured by the method of H. Diamant et al. (Rev. Sci. Instr., 28, 30, 1957), using measurement cells having an electrode separation of 10 μm without an alignment layer.

The electrical response time was measured by applying a rectangular voltage of ± 100 volts to the above-described measurement cell and measuring the polarization reversal current. The electrical response time τ is defined as the time delay between voltage reversal and the maximum polarization current.

The helical twisting power (HTP) in a nematic phase was determined by the Grandjean-Cano method using a wedge cell (F. Grandjean, CR Acad. Sci. (Paris) 172, 71 (1921), R. Cano, Bull. Soc. Franc. Minèral. Crystallogr. XC (333 (1967)). The phase-conversion temperatures were determined using a polarizing microscope from the changes in texture on heating. By contrast, the melting point was determined using a DSC instrument. The phase-conversion temperatures between the phases

| nematic | (N or N*) |
| smectic C | ($S_C$ or $S_C$*) |
| smectic A | ($S_A$ or $S_A$*) |
| crystalline | (X) | are given in °C., and the values are between the phase codes in the phase sequence.

EXAMPLE 1

2-Fluoro-3-octyl-6-(4-octyloxyphenyl)pyrazine

1a 40.00 g (268.5 mmol) of 2,6-dichloropyrazine, 31.20 g (537.0 mmol) of potassium fluoride and 7.10 g (26.9 mmol) of 18-crown-6 are heated at 120° C. for 0.5 hours under atmospheric pressure and for 3 hours at a pressure of 160 mm/lHg, during which a colorless liquid distills over giving, after purification by vacuum distillation at a pressure of 160 mmHg, 22.59 g of 2-chloro-6-fluoropyrazine.

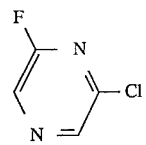

1b 7.99 g (60.0 mmol) of 2-chloro-6-fluoropyrazine, 15.08 g (60.0 mmol) of 4-octyloxyphenylboronic acid, 12.78 g (120.0 mmol) of sodium carbonate and 0.72 g (0.6 mmol) of tetrakis(triphenylphosphine)palladium(0) are heated at 80° C. for 2 hours in 400 ml of benzene, 300 ml of ethanol and 150 ml of water. The reaction mixture is partitioned between aqueous sodium chloride solution and ether, the organic phase is washed with aqueous sodium chloride solution, dried over sodium sulfate, filtered and freed from the solvents, and the residue is purified by chromatography (silica gel/hexane: ethyl acetate = 8:2). 17.18 g of 2-fluoro-6-(4-octyloxyphenyl)pyrazine are obtained.

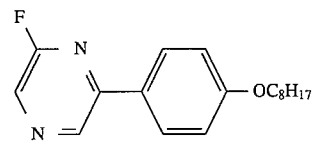

1c 3.50 g (24.8 mmol) of 2,2,6,6-tetramethylpiperidine and 15.50 ml (24.80 mmol) of 1.6 M n-butyllithium solution in hexane are stirred at 0° C. for 0.5 hour in 80 ml of tetrahydrofuran, 250 ml of tetrahydrofuran are added, and the mixture is cooled to −78° C. 5.00 g (16.5 mmol) of 2-fluoro-6-(4-octyloxyphenyl)pyrazine in 150 ml of tetrahydrofuran and, after the mixture has been stirred for one hour, 0.85 ml of bromine are subsequently added dropwise at −78C. The reaction mixture is stirred overnight, during which it warms to room temperature, and is partitioned between ether and aqueous sodium chloride solution, the aqueous phase is washed with aqueous sodium chloride solution, dried over sodium sulfate, filtered and freed from the solvent, and the residue is purified by chromatography (silica/hexane: ethyl acetate = 9:1). 4.68 g of 2-bromo-3-fluoro-5-(4-octyloxyphenyl)pyrazine are obtained.

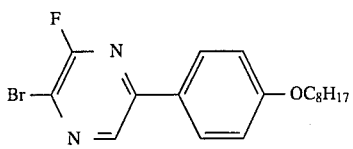

1d 7.95 mmol of freshly prepared octylmagnesium bromide in 30 ml of tetrahydrofuran are added dropwise at −10° C. to 2.00 g (5.3 mmol) of 2-bromo-3-fluoro-5-(4-octyloxyphenyl)pyrazine and 0.03 g (0.06 mmol) of [1,3-bis-(diphenylphosphino)propane]nickel(II) chloride in 30 ml of tetrahydrofuran, and the reaction mixture is stirred overnight, during which it warms to room temperature. The reaction mixture is partitioned between aqueous ammonium chloride solution and ether, the organic phase is washed with aqueous sodium chloride solution, dried over sodium sulfate, filtered and freed from the solvent, and the mixture is purified by chromatography (silica gel/dichloromethane: hexane = 7:3). 1.12 g of 2-fluoro-3-octyl-6-(4-octyloxyphenyl)pyrazine are obtained.

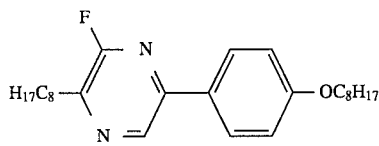

The compound has the following phase sequence:

X 42 S$_A$ 50 I

EXAMPLE 2

2-Fluoro-3,6-bis (4-octyloxyphenyl) pyrazine

An analogous reaction to Example 1b of 2.00 g (5.25 mmol) of 2-bromo-3-fluoro-5-(4-octyloxyphenyl)pyrazine (prepared as described in Example 1a–1c) and 1.31 g (5.25 mmol) of 4-octyloxyphenylboronic acid gives 1.96 g of 2-fluoro-3,6-bis (4-octyloxyphenyl)pyrazine.

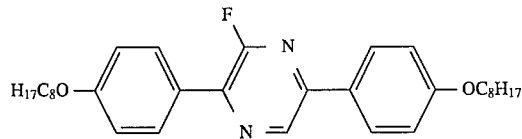

The compound has the following phase sequence:

X 89 S$_c$ 162 N 178 I

EXAMPLE 3

2-Fluoro-3-octyl-6-[4-(trans-4-pentylcyclohexyl)-phenyl]-pyrazine

3a

In an analogous reaction to Example 1b, 2.17 g (16.41 mmol) of 2-chloro-6-fluoropyrazine (prepared as described in Example 1a) and 4.50 g (16.41 mmol) of 4-(trans-4-pentylcyclohexyl)phenylboronic acid gives 3.36 g of 2-fluoro-6-[4-(trans-4-pentylcyclohexyl)-phenyl]pyrazine.

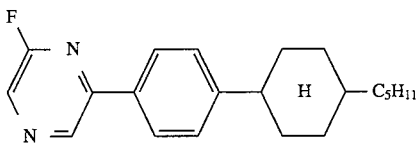

3b

In an analogous reaction to Example 1c, 3.10 g (9.50 mmol) of 2-fluoro-6-[4-(trans- 4-pentylcyclohexyl)-phenyl]pyrazine gives 2.75 g of 2-bromo-3-fluoro-5-[4-(trans-4-pentylcyclohexyl)phenyl]pyrazine.

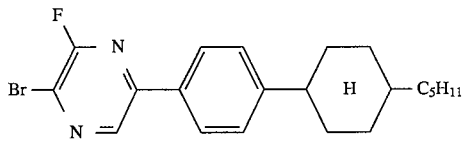

3c

In an analogous reaction to Example 1d, 2.75 g (6.80 mmol) of 2-bromo-3-fluoro-5-[4-(trans-4-pentylcyclohexyl)phenyl]pyrazine and 10.2 mmol of octylmagnesium bromide give 1.53 g of 2-fluoro-3-octyl-6-[4-(trans-4-pentylcyclohexyl)phenyl]pyrazine.

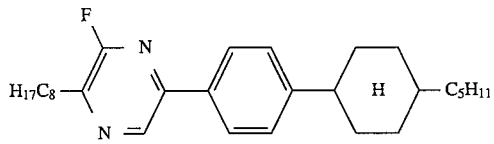

The compound has the following phase sequence:

X 48 S$_2$ 76 S$_A$ 128 I

EXAMPLE 4

4-(2-Fluoro-3-octylpyrazin-6-yl) phenyl trans-4-pentylcyclohexanecarboxylate

4a

In an analogous reaction to Example 1b, 8.86 g (66.85 mmol) of 2-chloro-6-fluoropyrazine (prepared as described in Example 1a) and 25.13 g (66.85 mmol) of 4-tert-butyldiphenylsilyloxyphenylboronic acid give 19.90 g of 2-fluoro-6-(4-tert-butyldiphenylsilyloxyphenyl)pyrazine.

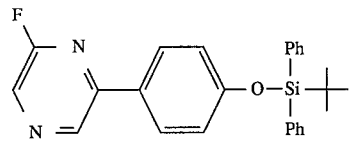

4b

In an analogous reaction to Example 1c, 5.00 g (35.00 mmol) of 2-fluoro-6-(4-tert-butyldiphenylsilyloxyphenyl)pyrazine give 15.57 g of 2-bromo-3-fluoro-5-(4-tert-butyldiphenylsilyloxyphenyl)pyrazine.

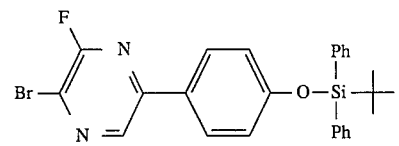

4c

In an analogous reaction to Example 1d, 15.57 g (30.70 mmol) of 2-bromo-3-fluoro-5-(4-tert-butyldiphenylsilyloxyghenyl)pyrazine and 46.00 mmol of octylmagneesium bromide give 11.82 g of 2-fluoro-3-octyl-6-(4-tert-butyldiphenylsilyloxyphenyl)pyrazine.

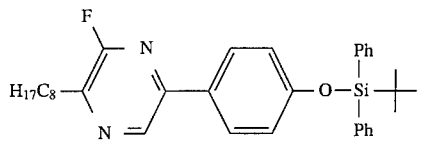

4d 11.82 g (21.87 mmol) of 2-fluoro-3-octyl-6-(4-tert-butyldiphenylsilyloxyphenyl)pyrazine and 43.74 ml of a 1 molar solution of tetra-n-butylammonium fluoride in tetrahydrofuran are stirred for 1 hour at room temperature in 140 ml of tetrahydrofuran. The reaction mixture is partitioned between aqueous sodium chloride solution and ether, the organic phase is washed with aqueous sodium chloride solution, dried over sodium sulfate, and freed from solvent, and the product is recrystallized from n-hexane. 6.00 g of 2-fluoro-3-octyl-6-(4-hydroxyphenyl) pyrazine are obtained.

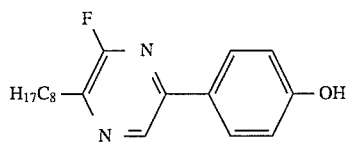

4e 2.00 g (7.00 mmol) of 2-fluoro-3-octyl-6-(4-hydroxyphenyl)pyrazine are stirred with 1.44 g (7.00 mmol) of dicyclohexylcarbodiimide and a little 4-dimethylaminopyridine for 6 hours at room temperature in 35 ml of dichloromethane. The solid constituents are filtered off, the mixture is freed from the solvent, and the residue is purified by chromatography (silica gel/hexane: ethyl acetate = 9:1) and by recrystallization from acetonitrile. 1.94 g of 4-(2-fluoro-3-octylpyrazin-6-yl)phenyl trans-4-pentylcyclohexanecarboxylate are obtained.

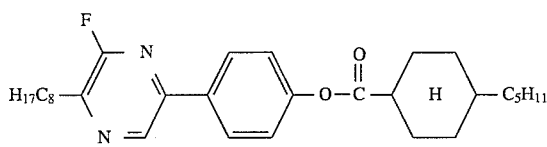

The compound has the following phase sequence:

X 58 S$_2$ 79 S$_A$ 157 I

EXAMPLE 5

2-Fluoro-3-octyl-6-[4-(4-butyldimethylsilylbutyloxy)-phenyl ]pyrazine

5a 1.82 ml (11.60 mmol) of diethyl azodicarboxylate are added dropwise at 0° C. to 3.04 g (11.60 mmol) of triphenylphosphine in 85 ml of tetrahydrofuran, and this mixture is stirred at 0° C. for 0.5 hour. 2.00 g (7.00 mmol) of 2-fluoro-3-octyl-6-(4-hydroxyphenyl)-pyrazine (prepared as described in Example 4a to 4d) and 2.46 g (11.60 mmol) of 4-butyldimethylsilylbutanol are subsequently added, and the mixture is stirred at room temperature for 3 hours. The reaction mixture is evaporated, and the residue is purified by chromatography (silica gel/dichloromethane: hexane = 8:2). 1.47 g of 2-fluoro-3-octyl-6-[4-(4-butyldimethylsilylbutyloxy)-phenyl-]pyrazine are obtained.

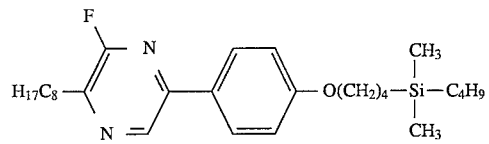

The refractive index η$^D$ of the compound is 1.5212 at 28° C.

EXAMPLE 6

[(2S, 3S)-3-Pentyloxiran-2-yl]methyl-4-(2-fluoro-3-octyl- pyrazin-6-yl)phenyl ether 6a In an analogous reaction to Example 5a, 3.04 g (11.60 mmol) of triphenylphosphine, 1.82 ml (11.60 mmol) of diethyl azodicarboxylate, 2.00 g (7.00 mmol) of 2-fluoro-3-octyl-6-(4-hydroxyphenyl)pyrazine and 1.67 g (11.60 mmol) of (2S,3S)-3-pentyloxiran-2-ylmethanol give 1.20 g of [(2S,3S)-3-pentyloxiran-2-yl]methyl 4-(2-fluoro-3-octylpyrazin-6-yl)phenyl ether of $[\alpha]_D^{20}$ (c = 0,995 in CHCl$_3$)=–16.58.

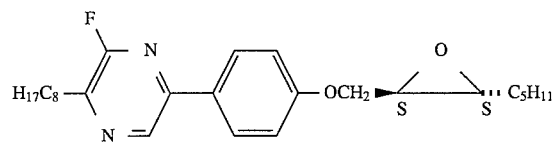

The compound has the following phase sequence:

X 64 S$_A$ 80 I

Use Example 1 a) A ferroelectric mixture comprising the components

| | |
|---|---|
| 5-octyloxy-2-(4-hexyloxyphenyl)pyrimidine | 22.8 mol % |
| 5-octyloxy-2-(4-butyloxyphenyl)pyrimidine | 24.0 mol % |
| 5-octyloxy-2-(4-decyloxyphenyl)pyrimidine | 19.2 mol % |
| 5-octyloxy-2-(4-octyloxyphenyl)pyrimidine | 10.5 mol % |
| 4-(5-pentylpyrimidin-2-yl)phenyl trans-4-pentylcyclohexanecarboxylate | 13.5 mol % |
| [(2S,3S)-3-pentyloxiran-2-yl]methyl 4-(2-fluoro-3-octylpyrazin-6-yl)phenyl ether | 10.0 mol % | has the following liquid-crystalline phase ranges:

S$_c$* 80 S$_A$ 94 N* 100 I

At a temperature of 20° C., it has a spontaneous polarization of 12.4 nC/cm$^2$ and switches with a response time of 212 µs at a field strength of 10 V/µm. In the nematic phase, the mixture has a helical twisting power (HTP) of between –0.45 µm$^{-1}$ and –0.39 µm$^{-1}$.

b) By comparison, a known liquid-crystalline mixture (DE 38 31 226.3) which differs from the above-mentioned mixture only in that it contains no dope has the following phase ranges:

S$_c$* 84 S$_A$ 93 N* 105 I

The mixture confirms that ferroelectric mixtures with fast response times can be prepared using the compounds according to the invention.

Use Example 2 a) A mixture which comprises the components

| | |
|---|---|
| 5-heptyl-2-(4-pentyloxyphenyl)pyrimidine | 9.48 mol % |
| 5-heptyl-2-(4-heptyloxyphenyl)pyrimidine | 14.23 mol % |
| 5-heptyl-2-(4-butyloxyphenyl)pyrimidine | 15.16 mol % |
| 5-(6-cyclopropyl)hexyloxy-2-(4-octyloxyphenyl)-pyrimidine | 14.38 mol % |
| trans-4-pentylcyclohexylmethyloxy [5-(8-cyclopropyloctyloxy)pyrimidin-2-yl]phenyl ether | 6.58 mol % |
| 5-(8-cyclopropyloctyl)pyrimidin-2-ylphenyl trans-4-pentylcyclohexanecarboxylate | 11.40 mol % |
| 5-octyl-2-[4-(6-cyclopropyl)hexylcarbonyloxy-phenyl]pyrimidine | 21.28 mol % |
| 2-fluoro-3-octyl-6-[4-(trans-4-pentylcyclohexyl)-phenyl]pyrazine | 7.5 mol % | has the following liquid-crystalline phase ranges:

$S_c$ 55 $S_A$ 74 N 94 I b) By comparison, the liquid-crystalline mixture which differs from the abovementioned mixture only in that it contains no compound according to the invention has the following phase ranges:

$S_c$ 61 N 91 I

The comparison shows that even when small amounts of the compound according to the invention are added to liquid-crystalline mixtures, an $S_A$ phase can be produced.

We claim:

1. A 2-fluoropyrazine of the formula (I)

$$R^1(-A^1)_k(-M^1)_l(-A^2)_m(-M^2)_n \text{—pyrazine ring with F}— (-M^3)_o(-A^3)_p(-M^4)_q(-A^4)_r-R^2 \quad (I)$$

in which the symbols have the following meanings:

$R^1$ and $R^2$ are, independently of one another, a straight-chain or branched alkyl having 1 to 16 carbon atoms (with or without an asymmetrical carbon atom), it also being possible for one or two non-adjacent —$CH_2$— groups each to be replaced by —O—, —CO—O—, —O—CO—, or —Si($CH_3$)$_2$—, and it also being possible for one or more hydrogen atoms of the alkyl radical each to be substituted by F, or one of the following chiral groups:

[chiral group structures with $R^3$, $R^4$, $M^5$]

$R^3-O-\overset{CH_3}{\underset{*|\ H}{C}}-CO-O-$, $R^3-O-CO-\overset{CH_3}{\underset{*|\ H}{C}}-O-$, $A^1$, $A^2$, $A^3$ and $A^4$ are identical or different 1,4-phenylene, it being possible for one or two hydrogen atoms each to be replaced by F, or are trans-1,4-cyclohexylene, $M^1$, $M^2$, $M^3$ and $M^4$ are identical or different —CO—O— or —O—CO—;

$R^3$ and $R^4$, independently of one another, are H or straight-chain or branched alkyl having 1 to 16 carbon atoms;

$M^5$ is —$CH_2$—O—, —CO—O—, —O—$CH_2$—, —O—CO— or a single bond; and k, l, m, n, o, p, q and r are zero or 1, with the condition that the sum of k+m+p+r is less than 3 and greater than zero.

2. A 2-fluoropyrazine as claimed in claim 1, wherein the symbols have the following meanings:

$R^1$ and $R^2$, independently of one another, are a straight-chain or branched alkyl having 1 to 16 carbon atoms (with or without an asymmetrical carbon atom), it also being possible for a —$CH_2$— group to be replaced by —O—, —CO—O—, —O—CO—, or —Si($CH_3$)$_2$—, or one of the following chiral groups:

[chiral group structures]

$R^3-O-\overset{CH_3}{\underset{*|\ H}{C}}-CO-O-$, $R^3-O-CO-\overset{CH_3}{\underset{*|\ H}{C}}-O-$, $A^2$, $A^2$, $A^3$ and $A^4$ are identical or different 1,4-phenylene, it being possible for one or two hydrogen atoms each to be replaced by F, or are trans-1,4-cyclohexylene, $M^1$, $M^2$, $M^3$ and $M^4$ are identical or different —CO—O— or —O—CO—;

$R^3$ and $R^4$, independently of one another, are H or straight-chain or branched alkyl having 1 to 16 carbon atoms; and $M^5$ is —$CH_2$—O—, —CO—O—, —O—$CH_2$—, —O—CO— or a single bond.

3. A 2-fluoropyrazine as claimed in claim 1, wherein the symbols have the following meanings:

$R^1$ and $R^2$, independently of one another, are a straight-chain or branched alkyl having 1 to 16 carbon atoms (with or without an asymmetrical carbon atom), it also being possible for a —$CH_2$— group to be replaced by —O—, —CO—O—, —O—CO—, or Si($CH_3$)$_2$—, or one of the following chiral groups:

[chiral group structures]

$R^3-O-\overset{CH_3}{\underset{*|\ H}{C}}-CO-O-$, $R^3-O-CO-\overset{CH_3}{\underset{*|\ H}{C}}-O-$, $A^1$, $A^2$, $A^3$ and $A^4$ are identical or different 1,4-phenylene, in which a hydrogen atom may be replaced by F, or are trans-1,4-cyclohexylene;

$M^1$, $M^2$, $M^3$ and $M^4$ are identical or different —CO—O— or —O—CO—;

$R^3$ and $R^4$, independently of one another, are H or straight-chain or branched alkyl having 1 to 16 carbon atoms; and $M^5$ is —$CH_2$—O—, —CO—O—, —O—$CH_2$—, —O—CO— or a single bond.

4. A 2-fluoropyrazine as claimed in claim 1, wherein symbols in the formula (I) have the following meanings: $R^1$ and R², independently of one another, are an alkyl having 1 to 16 carbon atoms, it being possible for a —CH₂— group to be replaced by —O—, or the chiral group

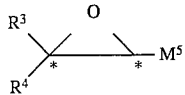

A¹, A², A³ and A⁴ are identical or different 1,4-phenylene or 1,4-cyclohexylene, M¹, M², M³ and M⁴ are —COO—, M⁵ is —CH₂O— or —COO—, and R³ and R⁴, independently of one another, are H or straight-chain alkyl having 1 to 10 carbon atoms.

5. A liquid-crystalline mixture comprising at least two components, wherein one component is a fluoropyrazine as claimed in claim 1.

6. A ferroelectric liquid-crystal mixture comprising 2 to 20 components, wherein one component is a compound as claimed in claim 1.

7. A nematic liquid-crystal mixture comprising 2 to 20 components, wherein one component is a compound as claimed in claim 1.

8. A ferroelectric liquid-crystal mixture comprising 2 to 20 components, wherein one component is a compound as claimed in claim 2.

9. A ferroelectric liquid-crystal mixture comprising 2 to 20 components, wherein one component is a compound as claimed in claim 3.

10. A ferroelectric liquid-crystal mixture comprising 2 to 20 components, wherein one component is a compound as claimed in claim 4.

11. A ferroelectric liquid-crystal mixture comprising 2 to 20 components, which contains from 1 to 25 mol % of at least one compound as claimed in formula (I) from claim 1.

12. A ferroelectric switching and display device containing outer plates, electrodes, at least one polarisor, at least one alignment layer and a liquid-crystalline medium, wherein the liquid-crystalline medium is a liquid-crystal mixture as claimed in claim 5.

13. A method for inducing or enlarging S$_A$ phases in liquid-crystalline mixtures, which comprises adding 1 to 25 mol % of at least one 2-fluoropyrazine of the formula (I), as claimed in claim 1, to a liquid-crystalline mixture comprising 2 to 20 components.

14. A 2-fluoropyrazine as claimed in claim 1, which is 2-fluoro-3-octyl-6-(4-octyloxyphenyl)pyrazine.

15. A 2-fluoropyrazine as claimed in claim 1, which is 2-fluoro-3,6-bis(4-octyloxyphenyl)pyrazine.

16. A 2-fluoropyrazine as claimed in claim 1, which is 2-fluoro-3-octyl-6-[4-(trans-4-pentylcyclohexyl)phenyl]-pyrazine.

* * * * *